(12) United States Patent
Beauvais et al.

(10) Patent No.: US 7,888,041 B2
(45) Date of Patent: Feb. 15, 2011

(54) **IN VITRO DIAGNOSTIC METHOD AND KIT FOR AN *ASPERGILLUS* INFECTION**

(75) Inventors: Anne Beauvais, Issy les Moulineaux (FR); Jean-Paul Debeaupuis, Le Vesinet (FR); Jean-Paul Latge, Issy les Moulineaux (FR); Sophie Paris, Paris (FR); Jacqueline Sarfati, Clamart (FR)

(73) Assignee: Institut Pasteur, Paris (FR)

( * ) Notice: Subject to any disclaimer, the term of this patent is extended or adjusted under 35 U.S.C. 154(b) by 315 days.

(21) Appl. No.: 11/988,038

(22) PCT Filed: Jun. 30, 2006

(86) PCT No.: PCT/IB2006/003039

§ 371 (c)(1),
(2), (4) Date: Dec. 28, 2007

(87) PCT Pub. No.: WO2007/015177

PCT Pub. Date: Feb. 8, 2007

(65) Prior Publication Data

US 2009/0305312 A1        Dec. 10, 2009

(30) Foreign Application Priority Data

Jul. 1, 2005    (EP) ................................. 05291428

(51) Int. Cl.
*G01N 33/53*    (2006.01)
*G01N 33/573*    (2006.01)

(52) U.S. Cl. .......................... 435/7.1; 435/7.4; 435/975

(58) Field of Classification Search ................. None
See application file for complete search history.

(56) References Cited

U.S. PATENT DOCUMENTS 5,185,252 A * 2/1993 Humphrey et al. .......... 435/134

\* cited by examiner

*Primary Examiner*—Mark Navarro
(74) *Attorney, Agent, or Firm*—Finnegan, Henderson, Farabow, Garrett & Dunner LLP

(57) ABSTRACT

The present invention relates to a method for the in vitro diagnosis of an *Aspergillus* infection by determining in the serum or plasma sample of a subject the quantity of antibodies directed against a combination of at least two of the ribonuclease (RNU), catalase (CA) and dipeptidylpeptidase V (DPPV) *Aspergillus* antigens. The invention also relates to a diagnostic kit comprising said combination.

31 Claims, 7 Drawing Sheets

IN VITRO DIAGNOSTIC METHOD AND KIT FOR AN *ASPERGILLUS* INFECTION

Figure 1:
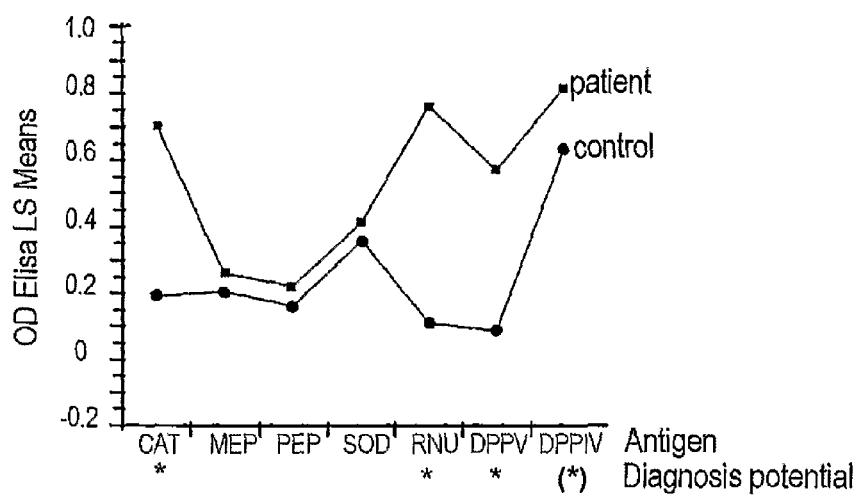

The present invention relates to a method for the in vitro diagnosis of an *Aspergillus* infection by determining in the serum or plasma sample of a subject the quantity of antibodies directed against a combination of at least two of the ribonuclease (RNU), catalase (CA) and dipeptidylpeptidase V (DPPV) *Aspergillus* antigens. The invention also relates to a diagnostic kit comprising said combination.

*Aspergillus fumigatus* is an opportunistic pathogen mat is responsible for a variety of infections in the immunocompetent as well as in the immunocompromised host. The successful management of the different forms of aspergillosis is often hampered by difficulties in establishing diagnosis in both type of patients. Diagnostic strategies are adapted to the immune status of the patient (Latgé J., Clin Microbiol Rev 1999; 12: 310-350). In the immunocompromised host and in patients with invasive aspergillosis, the "gold standard" for laboratory diagnosis is the search for circulating antigen. In the aspergillosis of the immunocompetent host, diagnosis is based on the presence of specific anti-*Aspergillus* antibodies.

The development of new, quantitative and reproducible assays for measuring the amount of anti-*Aspergillus* antibodies has shown recently a renewed interest for many reasons: (i) the number of patients with pre-existing cavities increases due to the revival of tuberculosis, lung carcinoma, emphysema and chronic obstructive broncho pneumopathy; these patients are at risk for aspergilloma and a serological survey remains clinically relevant for these patients that can contract serious clinically silent aspergilloma (Chu et al. 2004 J. Clin. Microbiol. 42:665-669; Denning, D. W. 1998. Clin. Infect. Dis. 26:781-803; Meersseman et al. 2004, Am. J. Respir. Crit. Care Med. 170:621-625); (ii) atopy to mould allergens worsens asthma severity; a recent study in the UK indicates that mold sensitization is associated with severe asthma attacks requiring hospital admission (Nelson et al., 1999, J. Allergy Clin. Immunol. 104:775-785; O'Driscoll et al., 1998, American Rev. Respir. Dis. 157:A623; Zureik et al., 2002, Bmj 325:411-414). Since it has been always a debate about the quantification of the skin prick tests or the presence of IgE-binding allergens shared by several fungi in the crude fungal extracts used in these tests, it become today relevant to quantify the sensitisation of asthmatic patients to *Aspergillus* allergens by the measurement of anti-*Aspergillus* antibody titers; (iii) ABPA is the most extreme manifestation of mold allergy occurring most often in the older cystic fibrosis patient population; since the age of this population at risk is continuously increasing and since ABPA remains a difficult complication to diagnose, a precise serological diagnosis would be the most helpful for this pathology (Stevens et al., 2003, Clin. Infect Dis. 3:S225-S264); (iv) finally, recent data suggest that antibody quantification could be also useful in the population of patients at risk for IA. The peak of occurrence of invasive aspergillosis in the immunocompromised population has been displaced in time to occur now towards sixth month after graft, at a time where the immune system is reinitialised (Morgan et al., 2004, Med. Mycol. 00:1-10). In addition, recent clinical surveys showed an increase in the incidence of IA in patients without hematologic malignancy in intensive care units (Meersseman et al., 2004, Am. J. Respir. Crit. Care Med. 170:621-625). IA in these relatively immunocompetent patients could be associated to an increase in antibody titers against *Aspergillus*. It has been also suggested (but never investigated) that patients could have been grafted while being colonized by *Aspergillus*. A high titer of antibody found prior to immunosuppression in patients to be grafted would suggest a pre-existing *Aspergillus* infection and could be an indication of mycological investigation and/or antifungal preventive treatment.

Antibody detection in patients with aspergillosis is still performed using crude antigens in semi quantitative methods such as immunoelectrophoresis, counterimmunoelectrophoresis or hemagglutination (Latgé et al., 1991, Infect Immun. 59:2586-2594). ELISA methods using in-house produced crude antigenic batches have been also introduced but the lack of standardisation between the different laboratories in charge of the diagnosis makes the comparison of the efficiency in aspergillosis diagnosis difficult to assess because of batch to batch variability.

Subjects with cystic fibrosis can become chronically colonised with *Aspergillus* fungus. *Aspergillus* fungus can act as an allergen and induces a hypersensitivity reaction within the lungs, giving rise to ABPA. The clinical features of ABPA may be masked or be mimicked by the respiratory symptoms of cystic fibrosis and is likely to result in an over-diagnosis. As many as 50% of cystic fibrosis subjects may have an isolated positive serological test at some time.

Invasive form of aspergillosis is becoming increasingly important in immunosuppressed conditions due to environmental pollution, enhanced use of chemotherapeutic drugs and antibiotics etc. The most susceptible hosts are the immunocompromised patients, such as cases with organ transplant, leukemia or human immunodeficiency virus (HIV) patients.

Earlier studies, in particular by the group of Crameri, has shown that reproducible quantification of anti-*Aspergillus* antibodies with immunochemical tests can be attained to date using recombinant antigens (Crameri R., *Chem Immunol* 2002; 81: 73-93; Crameri R, Kodzius R., *Comb Chem High Throughput Screen* 2001; 4: 145-155; Hemmann S. et al. *J Allergy Clin Immunol* 1999; 104: 601-607; Kodzius R. et al., *Comb Client High Throughput Screen* 2003; 6: 147-154; Kurup V P. et al., *Clin Exp Allergy* 2000; 30: 988-993). In the last 10 years, the inventors characterized several antigens of *Aspergillus fumigatus* among which the classical "chymotrypsic and catalase antigens" used since the studies of the Biguet's group in the diagnosis of aspergillosis or the antigen C of Longbottom (Beauvais A. et al. *J Biol Chem* 1997; 272: 6238-6244; Calera J A. et al. *Infect Immun* 1997; 65: 4718-4724; Kobayashi H. et al. *Infect Immun* 1993; 61: 4767-4771; Latgé J P. et al. *Infect Immun* 1991; 59: 2586-2594; Paris S. et al. *FEMS Microbiol Lett* 1993; 111: 31-36).

Despite these known *Aspergillus* antigens, there is to date no in vitro method for the diagnosis of an *Aspergillus* infection which is reproducible for every subject. Indeed, the level of antibodies directed against a given *Aspergillus* antigen varies with the subject, and the major diagnostic antigen is not the same from a subject to one another. This is probably due to the genetic variation in the B cell population of the different subjects; it may be also associated to fungal strains producing different amounts of the respective antigens in vivo.

Thus, there is a need for a new in vitro diagnosis method of an *Aspergillus* infection in a subject, which is effective and reproducible, whoever is the patient. The inventors have developed such a new method by selecting, among a plurality of *Aspergillus* antigens known from the skilled person, those which, when combined together, provide significant results allowing to conclude in a reliable manner that the subject suffers from an *Aspergillus* infection.

This method is appropriate for diagnosis of aspergilloma and ABPA. Differential diagnosis of ABPA is even possible among cystic fibrosis as well as non-cystic fibrosis patients, a very difficult task. The search of anti-*Aspergillus* antibodies may also be used to trace an *Aspergillus* primoinfection in patients waiting for immunosuppressive therapies.

In a first aspect, the invention relates to a method for the in vitro diagnosis of an *Aspergillus* infection by determining in the serum or plasma sample of a subject the quantity of antibodies directed against *Aspergillus* antigens, which comprises:

a) incubating said serum or plasma sample with the *Aspergillus* antigens for the formation of immunocomplexes susceptible to be obtained between said antibodies and said antigens, and b) determining the quantity of the antibodies directed against the *Aspergillus* antigens, wherein the *Aspergillus* antigens are selected from the group consisting of a combination of at least two the following antigens:

the ribonuclease (RNU) antigen,
the catalase (CA) antigen, and
the dipeptidylpeptidase V (DPPV) antigen.

In the present description, the terms "immunoglobulin" and "antibody" are used indifferently.

The RNU, CA and DPPV antigens are preferably obtained from *Aspergillus fumigatus*.

Any method well known from the skilled person may be used to obtain these antigens, such as by purification, by chemical synthesis (solid phase method) or by molecular biology using nucleic acids encoding said antigens and expression vectors (see below).

The term "subject" refers to any mammal, preferably a human being.

Preferably, at step (b), the determination of a significantly superior quantity of antibodies directed against at least one of said two antigens compared to the quantity obtained for a negative reference serum or plasma sample, is indicative of an *Aspergillus* infection.

The man skilled in the art is aware of how to determine the significantly superior quantity compared to that obtained for a negative reference serum or plasma sample. Usually, an appropriate statistical analysis will be used (see the Examples, in particular paragraph 6, "Antigen coating and ELISA" of the Examples). The significantly superior quantity will depend on the conditions which have been used in the method of the invention. The expression "negative reference serum or plasma sample" refers to any serum or plasma sample obtained from a subject not suffering from an *Aspergillus* infection.

The appropriate medium, appropriate conditions, and protocol for the formation of the immunocomplexes are known from the man skilled in the art working in the field of immunology. By way of example, various methods and protocols which can be used are described in "*Current Protocols in Immunology*" annually updated (4 volumes) and edited by the "National Institute of Health" by John E. Coligan, Ada M. Kruisbeek, David H. Margulies, Ethan M. Shevach, Warren Strober-Wiley Interscience.

Preferably, the *Aspergillus* antigens are coated on a solid support. Advantageously, each of said antigens is coated in a different location on the solid support.

The antigen coating may be realised on various solid supports known from the skilled person, preferably directly or indirectly using a spacer. The solid supports may include the glass, polystyrene, polypropylene, polyethylene, dextran, nylon or natural or modified celluloses. These supports may be soluble or insoluble. It may also consist in microbeads, an enzyme linked immunosorbent assay (ELISA) strip or in a microliter plate such as an (ELISA) plate.

By way of example, at step (a), the serum or plasma sample is incubated with the *Aspergillus* antigens which have been previously coated on a solid support. Then, the antibodies of the serum or plasma sample which have not formed immunocomplexes with the coated *Aspergillus* antigens are eliminated, for example with a washing buffer. In a following step, anti-immunoglobulin (anti-Ig) antibodies such as anti-IgG, anti-IgE and anti-IgA antibodies, conjugated with a marker may be contacted with the immunocomplexes formed on the solid support. The conjugated anti-Ig antibodies which have not interacted with the antibodies of the immunocomplexes are then eliminated. Finally, at the step (b), the quantity of said antibodies is determined by means of the detection signals obtained with the markers.

Markers which may be used are well known from the skilled person and may be selected from the enzymes, the dyes, the luminescent agents such as the radioluminescent (such as $^{14}C$, $^{36}Cl$, $^{57}Co$, $^{58}Co$, $^{51}Cr$, $^{152}Eu$, $^{59}Fe$, $^{3}H$, $^{125}I$, $^{131}I$, $^{32}P$, $^{35}S$, $^{75}SE$ and $^{99m}Tc$ which may be detected using for example gamma-ray counter or scintillation counter, autoradiography . . . ), bioluminescent, chimioluminescent (luminol, dioxetane, luciferase, luciferin), fluorescent, and phosphorescent agents, the ligands such as Worm, avidin, streptavidin, digoxygenin, 5-bromo-deoxyuridine, radioactive isotopes. Thus, the anti-Ig antibodies are conjugated for example with enzymes such as peroxydase, alkaline phosphatase, β-galactosidase, glucose oxydase, glucose amylase, anhydrase, acetylcholinesterase, lysozyme, la malate dehydrogenase or glucose-6 phosphate dehydrogenase. Fluorescent markers may be for example the fluorescein and its derived products, the fluorescein isothiocyanate (FITC), the allophycocyanin (APC), the phycoerythrin-cyanin 5 (PC5) and the phycoerythrine (PE), the calcein (AM), the red fluorescent tetramethyl-rhodamin or the rhodamin and its derived products, the GFP (Green Fluorescent Protein), the dansyl, the umbelliferone etc.

In a preferred embodiment, the solid support is an ELISA plate and the method comprises:

a) incubating said serum or plasma sample with the *Aspergillus* antigens coated on the ELISA plate, b) eliminating from the ELISA plate the antibodies of said serum or plasma sample not bound to the *Aspergillus* antigens, c) contacting anti-immunoglobulin (anti-Ig) antibodies conjugated with an enzyme, said anti-Ig antibodies being capable to bind to the antibodies of said serum or plasma sample, d) eliminating from the ELISA plate the anti-Ig antibodies not bound to the antibodies of said serum or plasma sample, e) adding the corresponding soluble substrate for the enzyme, and f) reading the absorbance values of the wells of the ELISA plate in an ELISA reader at an appropriate wavelength, wherein the quantity of said antibodies is determined by means of the obtained absorbance values.

The appropriate medium and conditions may be for example such as those applied below (see paragraph 6, "Antigen coating and ELISA" of the Examples).

Advantageously, the enzyme and corresponding soluble substrate are selected from the group comprising:

the alkaline phosphatase and the soluble substrate 4-nitrophenyl phosphate (PNPP);

the peroxidase and the soluble substrate orthophenylene diamine (OPD);

the β-galactosidase and the soluble substrate 2-nitrophenyl β-galactoside (ONPG); or the glucose-6-phosphate dehydrogenase and the soluble substrate glucose-6-phosphate (G6P).

In one embodiment, the *Aspergillus* antigens comprise the combination of the RNU and CA antigens. In another embodiment, the *Aspergillus* antigens comprise the combination of the RNU and DPPV antigens. In still another embodiment, the *Aspergillus* antigens comprise the combination of the CA and DPPV antigens. Most preferably, the *Aspergillus* antigens comprise the combination of the RNU, CA and DPPV antigens.

In addition to the *Aspergillus* antigens, the galactomannan (GM) antigen, a polysaccharidic antigen, may also be used. This GM antigen may be obtained by purification from an *Aspergillus* culture (see for example point 3: "Purification of galactomannan", in part I: "Material and methods"), or by any other method well known by the man skilled in the art.

Advantageously, each of the RNU, CA, DPPV and GM antigens is coated on the solid support at a density ranging from 0.1 to 10 µg/mL, more advantageously 1 µg/mL.

In a further preferred embodiment, at least one of the RNU, CA and DPPV *Aspergillus* antigens, is a recombinant antigen. Advantageously at least two of the RNU, CA and DPPV *Aspergillus* antigens are recombinant antigens. Most advantageously, the three RNU, CA and DPPV *Aspergillus* antigens are recombinant antigens.

Preferably, the at least one recombinant *Aspergillus* antigen is obtained by cloning the amplification product of the corresponding cDNA in an expression vector. More preferably, the amplification product of the corresponding cDNA is obtained from an *Aspergillus fumigatus* cDNA library using a couple of primers specific for said at least one *Aspergillus* antigen.

The skilled person has at his disposal the molecular and cellular biology tools to realise the cloning and recombinant expression of the RNU, CA and DPPV antigens (see, for example, Sambrook et al., Molecular Cloning: A Laboratory Manual, Cold Spring Harbor Laboratory, Cold Spring Harbor, N.Y. (1989) and Ausubel et al., Current Protocols in Molecular Biology, J. Wiley & Sons, NY (1992)). A wide variety of expression host/vector combinations may be employed, such as bacterial hosts and corresponding known bacterial plasmids, yeast cells/yeast expression vectors, insect cells/insect expression vectors, mammals cells/mammal expression vectors, etc. . . . . In addition, any suitable expression control sequence may be used in these vectors.

Preferably, said at least one recombinant *Aspergillus* antigen is obtained using *Pichia pastoris* yeast, such as GS115 and KM71 yeast strains, and suitable expression vectors, such as pKJ111 (Monod M. et al, *Contrib Microbiol* 1999; 2: 182-192), pKJ113 (Borg-von Zepelin M. et al, *Mol Microbiol* 1998; 28: 543-554), pHILS1 and pPICZαA (Invitrogen).

The cDNA library which may be used is the *Aspergillus fumigatus* λgt11 cDNA library of Monod M. et al (1991).

Advantageously, the couple of primers specific for the RNU antigen is SEQ ID No 1 and SEQ ID No 2. More advantageously, the couple of primers specific for the CA antigen is SEQ ID No 3 and SEQ ID No 4. Most advantageously, the couple of primers specific for the DPPV antigen is SEQ ID No 5 and SEQ ID No 6.

In another preferred embodiment a unique profile of detection signals for a given *Aspergillus* strain is determined.

More preferably, the method of the invention further comprises comparing the detection signal profile with a standard profile for each *Aspergillus* strain, allowing identification of the strain infecting the subject.

Preferably, the *Aspergillus* infection has led to aspergilloma and/or allergic bronchopulmonary *Aspergillus* (ABPA).

Aspergilloma is a characteristic pulmonary lesion caused by a mass of mycelial elements of *Aspergillus* fungus, forming a spheroidal mass within a fibrous-walled lung cavity which is usually continuous with a bronchus.

More preferably, the *Aspergillus* infection leading to ABPA is diagnosed in a subject suffering from cystic fibrosis as well as in a subject not suffering from cystic fibrosis.

Advantageously, the *Aspergillus* infection is an invasive aspergillosis which it is possible to diagnose before immunosuppression in the subject to be grafted.

More advantageously, allows the diagnosis of the *Aspergillus* infection in an immunocompromised human being, advantageously in an human immunodeficiency virus (HIV) human being.

In a second aspect, the invention relates to a diagnostic kit for determining in a serum or plasma sample the quantity of antibodies directed against *Aspergillus* antigens, comprising:
(a) a combination of at least two of the following *Aspergillus* antigens:
the RNU antigen,
the CA antigen, and
the DPPV antigen.

Preferably, the diagnostic kit of the invention further comprises a solid support wherein said *Aspergillus* antigens are coated. Advantageously, each of said antigens is coated in a different location on the solid support.

Advantageously, the diagnostic kit further comprises:
(b) a solution containing anti-Ig antibodies conjugated with a marker.

More advantageously, the diagnostic kit further comprises:
(c) a washing buffer.

In one embodiment, the *Aspergillus* antigens comprise the combination of the RNU and CA antigens. In another embodiment, the *Aspergillus* antigens comprise the combination of the RNU and DPPV antigens. In still another embodiment, the *Aspergillus* antigens comprise the combination of the CA and DPPV antigens. Most preferably, the *Aspergillus* antigens of the diagnostic kit comprise the combination of the RNU, CA and DPPV antigens.

In a further embodiment, the *Aspergillus* antigens of the diagnostic kit additionally comprise the GM antigen.

Advantageously, each of the RNU, CA, DPPV and GM antigens is coated on the solid support at a density ranging from 0.1 to 10 µg/mL, more advantageously 1 µg/mL.

In a further preferred embodiment, at least one of the RNU, CA and DPPV *Aspergillus* antigens, is a recombinant antigen. Advantageously at least two of the RNU, CA and DPPV *Aspergillus* antigens are recombinant antigens. Most advantageously, the three RNU, CA and DPPV *Aspergillus* antigens are recombinant antigens.

In a preferred embodiment, the solid support is an ELISA plate and the marker is an enzyme.

In a more preferred embodiment, the diagnostic kit further comprises:
(d) a solution containing the corresponding soluble substrate for the enzyme.

In a third aspect, the invention relates to the use of a combination of at least two of the following antigens for the diagnosis of m *Aspergillus* infection in a human being:
the RNU antigen,
the CA antigen, and
the DPPV antigen.

Preferably, the combination is that of the RNU, CA and DPPV antigens.

In another preferred embodiment, an ELISA test is used for the diagnosis.

A further preferred embodiment is the use of the invention wherein the *Aspergillus* infection has led to aspergilloma and/or allergic bronchopulmonary *Aspergillus* (ABPA). Preferably, the *Aspergillus* infection leading to ABPA is diagnosed in a subject suffering from cystic fibrosis as well as in a subject not suffering from cystic fibrosis.

In another preferred embodiment, the *Aspergillus* infection is an invasive aspergillosis which it is possible to diagnose before immunosuppression in a human being to be grafted.

In another preferred embodiment, the use of the invention allows me diagnosis of the *Aspergillus* infection in an immunocompromised human being, advantageously in a human immunodeficiency virus (HIV) human being.

The present invention is further described in the following examples. These examples are provided for purposes of illustration only, and are not intended to be limiting the scope of the appended claims. The various scenarios are relevant for many practical situations, and are intended to be merely exemplary to those skilled in the art. Thus, the invention should be construed to encompass any and all variations that become evident as a result of the teaching provided herein.

LEGENDS OF THE FIGURES

FIG. 1. Antibody response directed against 7 recombinant antigens in sera of aspergilloma and control patients. Values shown are the means of optical densities (OD) ELISA from 57 patients and 41 controls from 3 centers (1 serum per patient). OD values obtained with antigens followed by an asterisk in the "Diagnostic potential" line are significantly different in a 3 way ANOVA variance analysis with center, antigen and pathology as factors (DPPIV is only significant in one of the centers).

Figure 2:
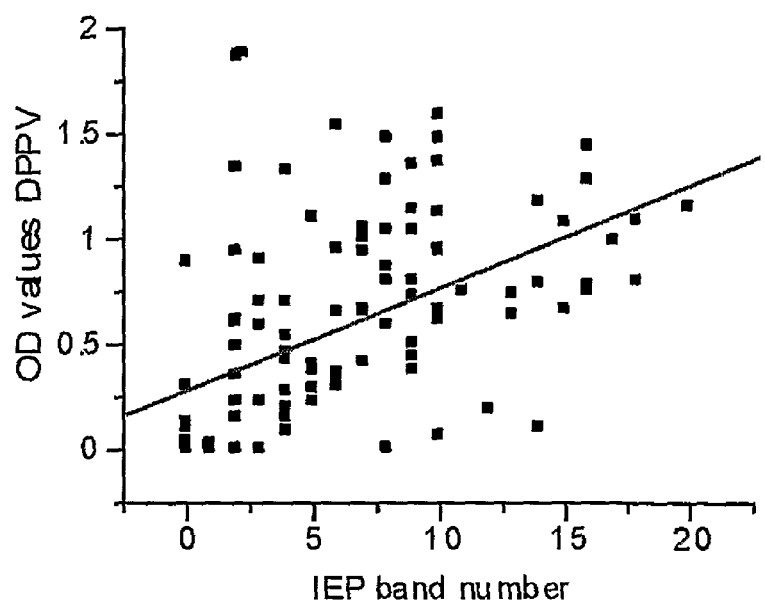

FIG. 2. Correlation between the number of IEP bands and the anti-DPPV antibody level (expressed in OD value). The linear fit (OD DPPV=0.3+0.05 IEP band numbers) is statistically significant (p<0.0001 for an error df of 101).

Figure 3:
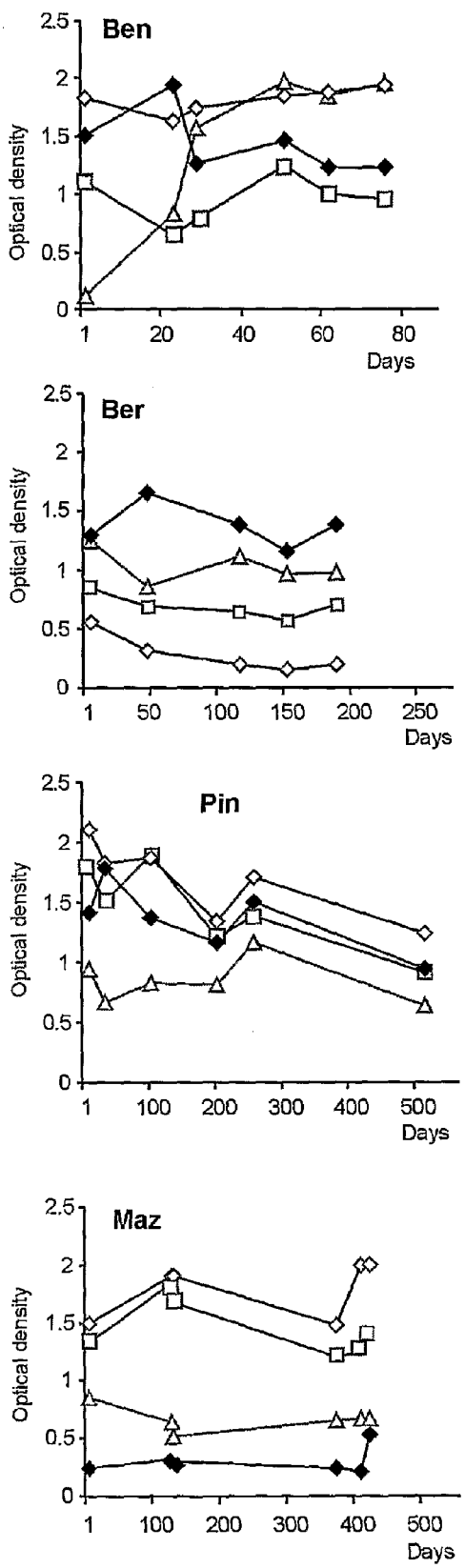

FIG. 3. Follow up of antibody levels directed against CAT, RNU, DPPV and GM in the sera of 4 aspergilloma patients (Ben, Ber, Pin, Maz). Anti-recombinant antigen antibody levels are expressed in OD values; CAT=☐; DPPV=◇; RNU=△; GM=◆

Figure 4:
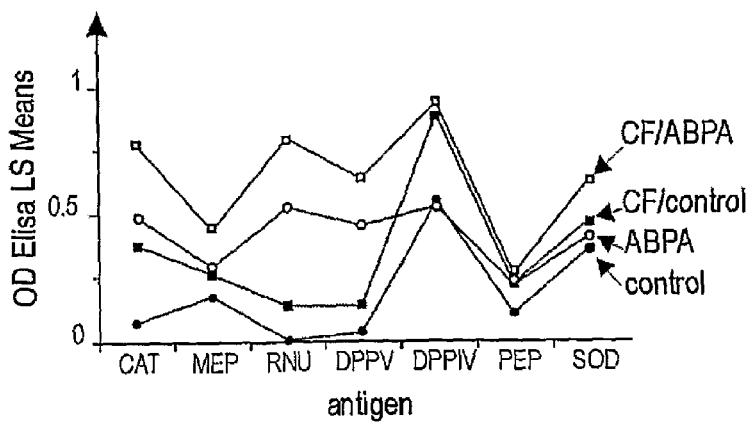

FIG. 4. Antibody response against 7 recombinant antigens by ABPA patients and their respective atopic or cystic fibrosis control counter parts. OD values shown are means of 12 ABPA and 16 ABPA/cystic fibrosis and 51 cystic fibrosis and 37 control patients (1 serum per patient, 2 centers). Significativity of the data is shown in Table 3.

Figure 5:
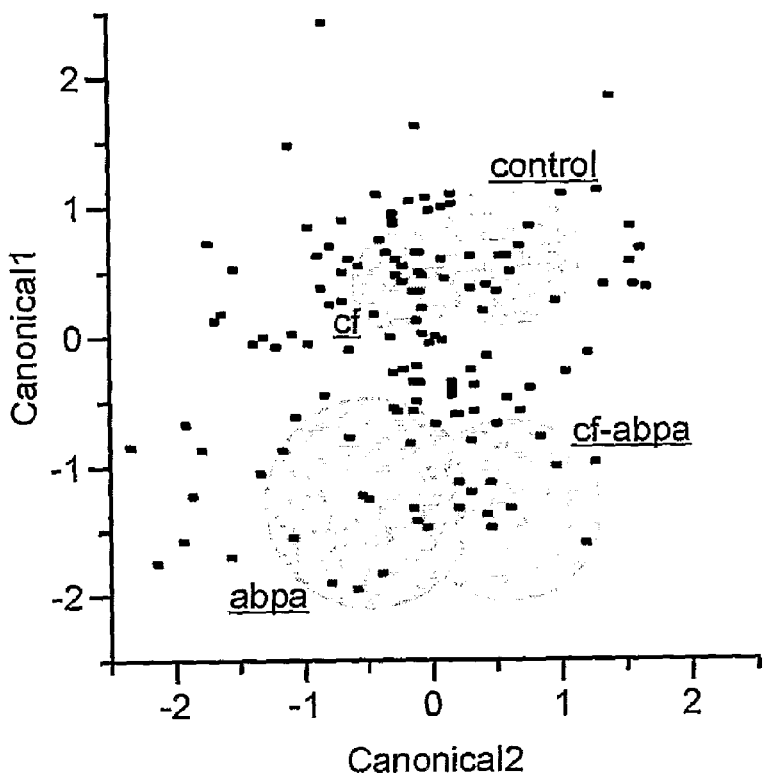

FIG. 5. Canonical plot showing the separation of the ABPA populations with their respective controls. For the discriminant analysis, the OD values obtained with all recombinant antigens have been used. Canonical plot shows the points and multivariate means in the two dimensions that best separate the groups of patients. The size of the circle corresponds to a 95% confidence limit for the mean. Groups that are significantly different tend to have non-intersecting circles.

Figure 6:
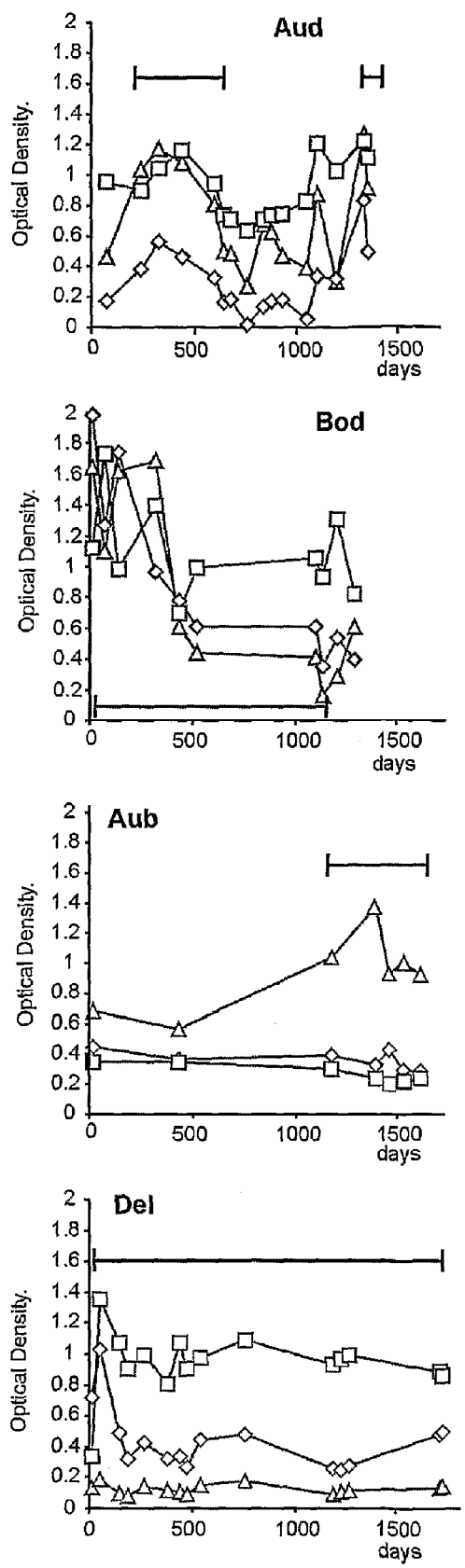

FIG. 6. Follow up of antibody levels directed against CAT, RNU and DPPV in the sera of 4 ABPA patients (Aud, Bod, Aub, Del). Anti-recombinant antigen antibody levels are expressed in OD values. Bars indicates the ABPA period as defined by the clinician. (CAT=☐; DPPV=◇; RNU=△).

Figure 7:
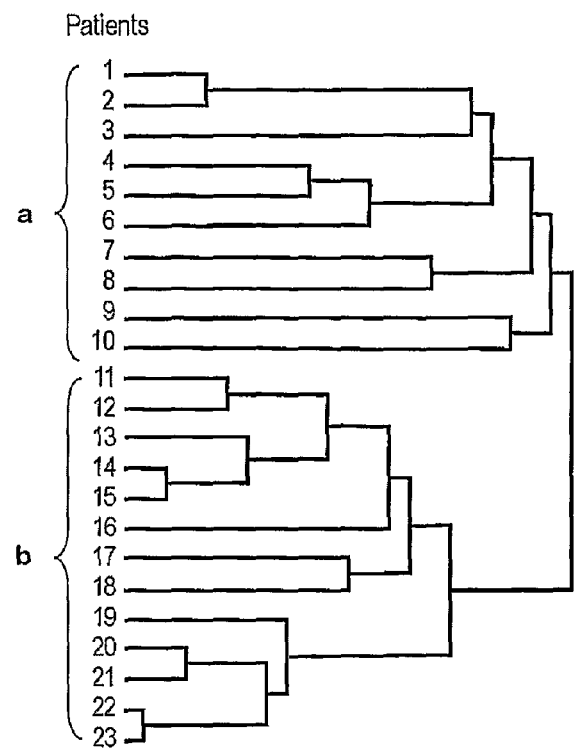

FIG. 7. Hierarchical clustering (Ward method) of 23 patients with proven IA. Clustering has been based on the OD values obtained by ELISA with CAT and DPPV antigens in sera taken at the entrance of patients at the hospital; a: patients with high antibody titers; b: patients with low antibody titers.

Figure 8:
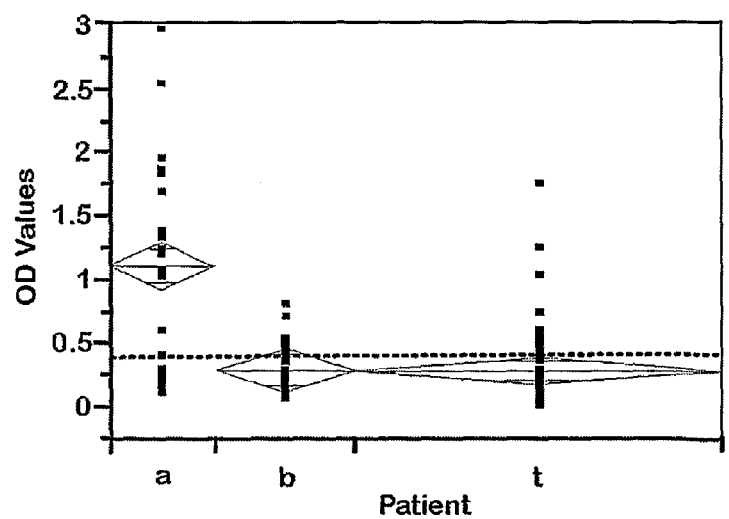

FIG. 8. One way variance analysis showing that the population of IA patients with high titer of antibodies (a) before graft were different from the populations of patient b and control population (see FIG. 7 for the clustering of the patients). Diamond means indicate the sample mean and 95% confidence interval. Circles visualise the Student's pair analysis: the significativity of the results is indicated by the lack of intersection between two circles.

Figure 9:
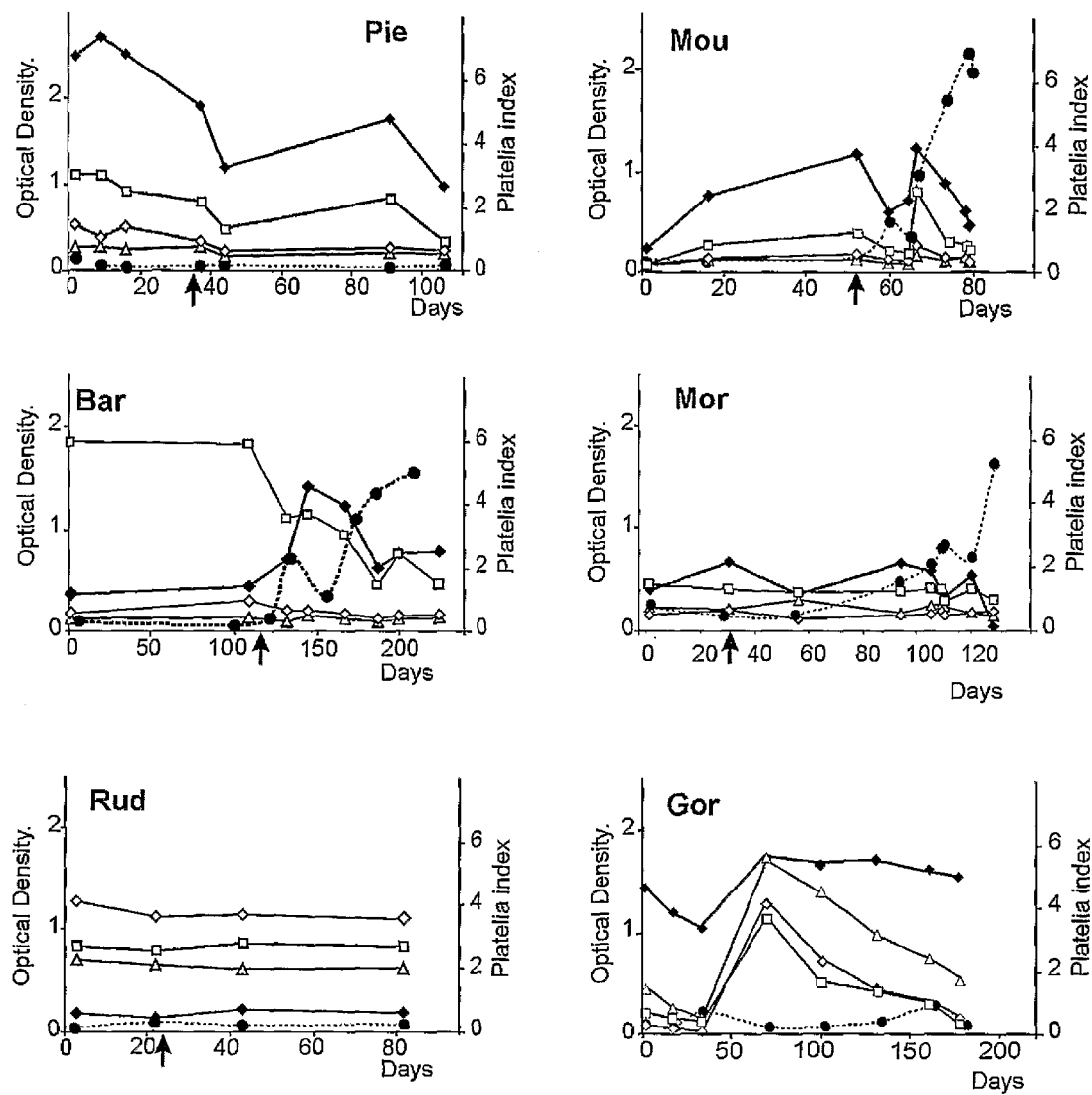

FIG. 9. Evolution of antibodies titers against RNU, CAT, DPPV, GM and GM antigen in six patients with proven IA. Day 0 is the first sample taken at the entrance of the patient to the hospital. Graft (when performed) is indicated by an arrow. Patients PIE, BAR and RUD belong to the a cluster (see FIG. 7) characterized by high antibody levels directed against DPPV and CAT. Patients MOU, MOR and GOR belong to the cluster b of patients with low levels of antigens against CAT and DPPV CAT=☐; DPPV=◇; RNU=△; GM=◆; GMAg ●

Figure 10:
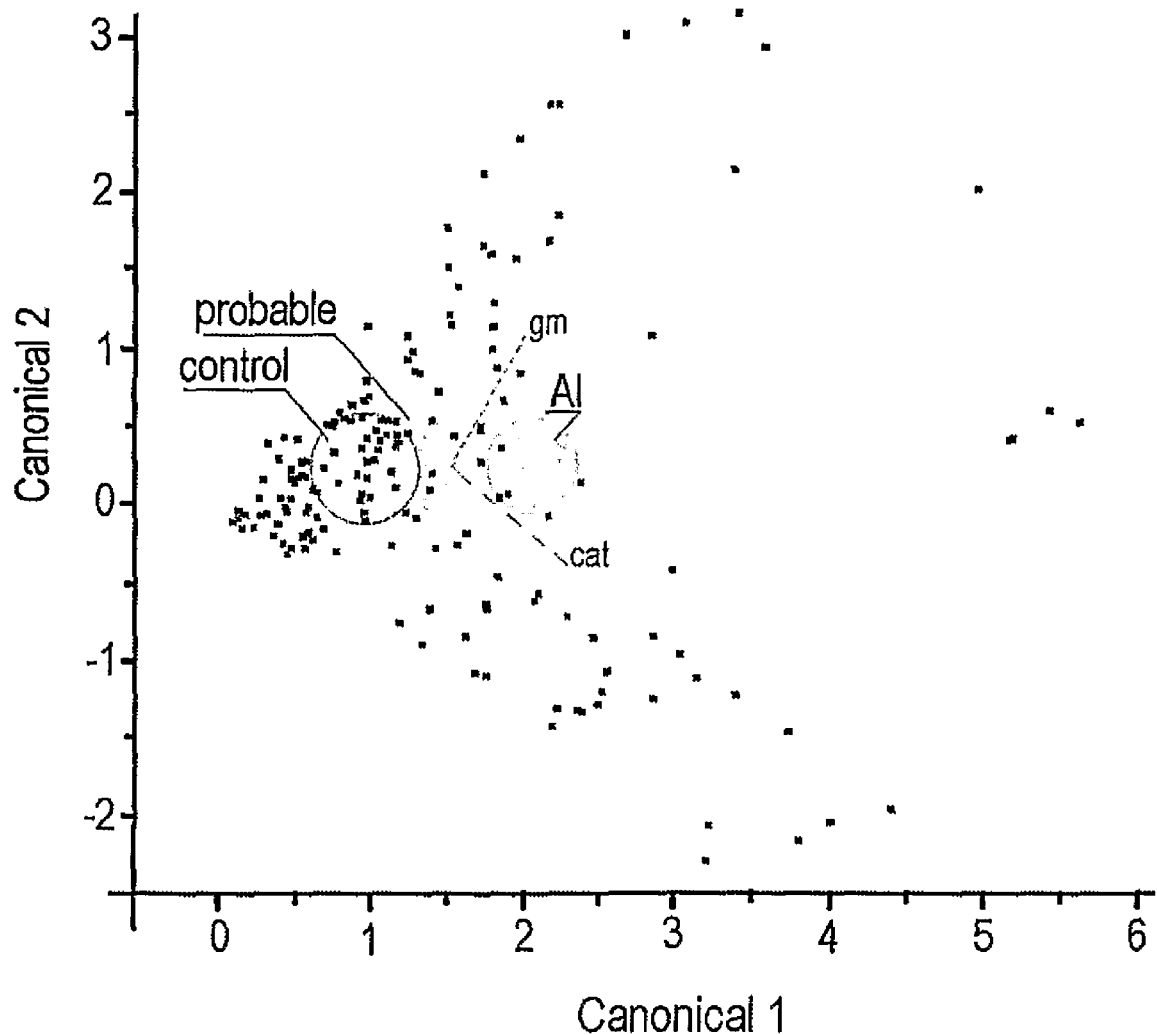

FIG. 10. Canonical plot showing the 3 populations of patients (certain, probable IA or negative) discriminated with antibody levels at their entrance in the hospital. For the discriminant analysis, the OD values obtained with DPPV, GM, RNU and CAT antigens have been used. Canonical plot shows the points and multivariate means in the two dimensions that best separate the groups of patients. The size of the circle correspond to a 95% confidence limit for the mean. Groups that are significantly different tend to have non-intersecting circles.

EXAMPLES

I. Material and Methods

1. Strains and Plasmids

The strain of *A. fumigatus* used is the strain CBS 144.89 of clinical origin. *Pichia pastoris* GS115 and KM71 and the expression vectors pKJ111 (Monod M. et al, 1999), pKJ113 (Borg-von Zepelin M. et al, 1998), pHILS1 and pPICZαA (Invitrogen) were used to express recombinant antigens. All plasmid cloning experiments were performed in *E. coli* XL1 blue. *E. coli* LE392 was used for the propagation of the bacteriophage λgt11 (Promega).

2. Production of Recombinant Polypeptides

*A. fumigatus* antigens cDNAs were obtained by PCR using DNA prepared from $10^6$ clones of a λgt11 cDNA library previously constructed (Monod M. et al, 1991). Primers were derived from genomic DNA sequences of the genes coding for the alkaline protease ALP (Monod M. et al., 1993, FEMS Microbiol Lett. 106:39-46), metalloprotease MEP (Jaton-Ogay et al., 1994, Mol. Microbiol. 14:917-928), aspartic protease PEP (Reichard et al., 1995, FEMS Microbiol. Lett. 130:69-74), ribonuclease RNU (Paris et al., 1993, FEMS Microbiol. Lett. 111:31-36), superoxide dismutase SOD (Holdom et al., 2000, J. Clin. Microbiol. 38:558-562), catalase CAT (Calera et al., 1997, Infect. Immun. 65:4718-4724), dipeptidylpeptide IV DPPIV (Beauvais et al., 1997, Infect Imm. 65:3042-3047) and dipeptidylpeptidase V DPPV (Beauvais et al., 1997, J. Biol. Chem.: 6238-6244) (Table 1). Two hundred ng of target DNA, 10 µl of each sense and antisense oligonucleotides at a concentration of 42 mM and 8 µl of deoxynucleotide mix (containing 10 mM of each dNTP) were dissolved in 100 µl PCR buffer (10 mM Tris-HCl pH 8.3, 50 mM KCl and 1.5 mM $MgCl_2$). To each reaction 2.5 U of AmpliTAQ DNA polymerase (Perkin Elmer) were added. The reaction mixtures was incubated 5 min at 94° C., subjected to 25 cycles of 0.5 min at 94° C., 0.5 min at 55° C. and 0.5 min at 72° C. and finally incubated 10 min at 72° C.

Expression plasmids were constructed by cloning cDNA PCR products in *P. pastoris* expression vectors. The PCR products were purified using a PCR purification kit (Roche Diagnostics) and digested by restriction enzymes for which a site was previously designed at the 5' end of the primers (Table 1). *P. pastoris* transformation, selection of transformants and production of recombinant enzymes in methanol medium were performed as previously described (Beggah S. et al., *Microbiology* 2000; 146: 2765-2773; Borg-von Zepelin M. et al., 1998). All 6× His-tagged (SEQ ID NO: 33) proteins bound to a Probond column (Invitrogen) with the exception of the DPPIV. After washing the column with a 20 mM phosphate pH6 buffer containing 0.5 M NaCl, the proteins were eluted from the Ni 2+ column with 50 mM Histidine. Elution of RNU required the use of 500 mM Imidazole buffer pH and the protein was dialysed against 50 mM Histidine solution. The solubilization of the different antigens in the 50 mM Histidine solution allowed a direct coating of the antigens on the Microtiter plate whereas Imidazole interfered with coating and subsequent colorimetric reaction (data not shown).

In contrast to the other antigens, the DPPIV did not bind to the Ni 2+ column. Western blot analysis of the DPPIV with an anti-polyhistidine clone His1 monoclonal antibody (Sigma) diluted 1/1000 was negative whereas a DPPV control was positive (data not shown). This result showed that the lack of binding to the Ni column was not due to the lack of accessibility of the 6 His Tag (SEQ ID NO: 33) to the Ni because of a specific three dimensional structure of the protein, but to the absence of the sequence coding for the 6His Tag (SEQ ID NO: 33) in the DPPIV recombinant protein. Purification of the DPPIVp was done as described earlier (Beauvais A. et al. *Infect Imm* 1997; 65: 3042-3047) with some modifications. To purify the DPPIVp, the culture filtrate of *Pichia* was precipitated by 4 vol. of EtOH and the precipitate solubilized in water was dialysed against 20 mM Tris HCl buffer pH 8.0. Proteins were loaded on a MonoQ HR 5/5 column and the protein eluted with a 0-500 mM NaCl. Fractions containing the dipeptidylpeptidase activity measured as described previously (Beauvais A. et al., 1997) were pooled together and concentrated under vacuum. Final purification was performed using a Superdex 200 HR 10/30 gel permeation column using a 20 mM TrisHCl buffer pH 8.0 containing 0.12 M NaCl. It was verified that the protein purified had the dipeptidylpeptidase activity described earlier (Beauvais A. et al., 1997).

The purity of the different batches of antigens was controlled by the lack of contaminating protein band in SDS PAGE after overloading a 10% separating acrylamide gel.

3. Purification of Galactomannan (GM).

*A. fumigatus* was grown for 40 hours in a fermenter as described previously (Hearn et al., 1990, In R. A. Samson and J. I. Pitt (ed.), Modern concepts in *Penicillum* and *Aspergillus* classification, Plenum Press, London, New York). Due to the termination of the commercialisation of hydrazine, another protocol of purification of the GM was undertaken. The culture filtrate was ethanol-precipitated and the precipitate was first digested for 3 days at 37° C. with amylase (from *Bacillus licheniformis*, Ref Sigma A4551) at a 1:30 ratio (dry weight) in 100 mM Na acetate buffer pH 5.6 and then incubated 3 days at 37° C. with Pronase (from *Streptomyces griseus*, Ref Sigma P5147) at a 1:6 ratio (dry weight). The reaction mixture was boiled 10 min at 100° C. and further treated for 1 hour at 60° C. in presence of NaOH (1M final concentration). After neutralisation, the GM was dialysed and freeze dried. The purity of GM was verified by Gas chromatography as previously described (Fontaine et al., 2000, J. Biol. Chem. 275:27594-27607, Latgé et al., 1994, Infect. Immun. 62:5424-5433).

4. Patients

Pathologies were identified on each center based on clinical symptoms with rules established in each hospital. 57 aspergilloma patients and 41 controls were recruited in 3 centers (Toulouse, Grenoble and Strasbourg). In addition, 2 to 9 (average, 3.9) samples were taken sequentially per patient in the center of Toulouse. In the centers of Toulouse and Grenoble, 16 ABPA patients and 51 controls in the cystic fibrosis population were analysed. 12 ABPA in a non-cystic fibrosis population were compared to 27 controls. In Toulouse, sequential samples (3 to 16, average of 8.6) per patients were available for 14 ABPA patients (in a cystic fibrosis or non-cystic fibrosis background). All IA patients were from hospital StLouis (Paris): 23 with proven or probable IA, 21 with possible IA and 34 controls that were immunosuppressed or/and grafted as the IA patients. For each series of patients, 1- to 5 samples (average 7.5), 2 to 11 samples (average 6) and 1 to 12 samples (average 3.9) were available per patient with proven/probable IA, possible IA and control patient respectively. One to 7 sera per patient were also available before graft or start of the immunosuppressive therapy.

5. Immuno-Electrophoresis (IEP)

Fast IEP was performed using the Beckman-IEP Paragon system following an adaptation of the manufacturer instructions. Briefly, migration of the somatic and metabolic *Aspergillus* antigens (Sanofi Pasteur Diagnosis, Marnes la Coquette, France) was performed at 100V for 12 min. Incubation with the neat serum lasted for 18-24 hrs. After sodium citrate washings, the presence of a precipitin with catalase activity was visualised with 3% $H_2O_2$ and the total number of precipitins was counted after Coomassie Blue or Paragon Violet Acid staining of the dried gel.

6. Antigen Coating and ELISA

All protein antigens and galactomannan were coated on ELISA plates (Greiner Ref. 762070) at a concentration of 1μ for all antigens except the catalase that was coated at 4 μg/ml. After coating, the wells were emptied and filled with 300 μl of PBS supplemented with 2% Tween 20. After 1-hr incubation at room temperature, the PBS/Tween solution was replaced by 300 μl of PBS containing 5% glucose and 2.5% defatted milk and the plates incubated for 2 min at RT. The wells were emptied again and dried in ah oven at 60° C. for 10 min. After drying, plates were stored frozen. Coating antigen concentrations and protocols were based on preliminary experiments that indicated that these concentrations ensured optimal OD readings with a pool of sera from aspergilloma patients known to contain high amounts of anti-*Aspergillus* antibodies. Patient sera were diluted 1/500 in PBS containing 0.05% Tween 20 and 1% BSA. The sera from Toulouse and St Louis were analysed in the inventors' laboratory. The sera from Grenoble and Strasbourg were tested on site according to the protocol followed at Pasteur which contained classically the following steps: Incubation for 1 h at 37° C. with the patient serum; 5 washings with PBS Tween 20 0.05%; incubation with a secondary anti IgG (H+ L) antibody conjugated to peroxidase (Sigma); 5 washings and incubation with ortho-phenylene diamine (OPD) for OD readings. Experiments were done in duplicate and repeated at least once.

7. Statistical Analysis

Statistical analysis of the data was performed using the JMP software (SAS, Cary, N.C.). Mean values were calculated and the standard error computed. Methods used were variance analysis followed by ranking of the means using the least square means differences analysed by the Student's t test Bivariate analysis to analyse the distribution of one continuous variable to another one was done through the density ellipse fitting using the Pearson correlation r value for significativity. Discriminant analysis classified OD values for antigen into groups of patients predefined on the basis of their pathology. Analysis was presented as a canonical plot showing the points and multivariate means in the two dimensions that best separate the groups. Sensitivity, specificity, negative predictive values and positive predictive values were estimated based on optimised cut off values calculated from control patients.

II. Results

1. Aspergilloma

FIG. 1 shows that among the protein antigens, the DPPV, catalase and ribonuclease antigens produced the best discrimination between patients and controls. In spite of high levels of antibodies in the control sera, DPPIV was also useful to identify aspergilloma patients. In contrast, the proteases (aspartic, metallo and serine-proteases) and the superoxide dismutase did not induce a specific humoral response in aspergilloma patients (data not shown for serine protease). A 3 way variance analysis showed a significant response (p= 0.03) for the interaction factor center×antigen×pathology. This was due to the response towards DPPIV that was discriminative with patients from Toulouse but was not in the other centers (data not shown). In contrast, the discriminative efficiency of the ribonuclease, dipeptidylpeptidase and catalase was good in the 3 centers. Anti-RNU, anti-CAT and anti-DPPV antibody levels were significantly higher in the patient populations than in the control population of all three centers tested. Table 2 shows that the sensitivity of the test increased with the number of antigens included in the test; a maximal value of 95% was reached when the OD values obtained with the 3 antigens were computed. In contrast, the specificity values slightly decreased when multiple antigens were used.

A detailed analysis of the patients of the center of Toulouse was undertaken since the inventors had multiple sequential samples per patient. In this series of patients, the galactomannan (GM) antigen was also tested and compared to RNU, CAT and DPPV, the 3 discriminative recombinant protein antigens shown above to be discriminative. ELISA OD values showed that the galactomannan antigen was also discriminative for this pathology. The OD average for control patients was higher with the GM and CAT antigens than with RNU and DPPV. Under the conditions tested, average OD values of 0.82±0.05, 0.95±0.08, 1.0±0.07 and 0.71±0.04 were obtained respectively with RNU, DPPV, GM and CAT in the sera of the aspergilloma patients whereas these values were 0.26±0.07, 0.25±0.06, 0.74±0.06 and 0.47±0.09 in the sera of the control patients. A good correlation score was obtained for all antigens with the best correlation obtained with antigens GM, CAT and DPPV. Moreover, bivariate analysis show a good and statistically significant correlation between the numbers of IEP bands obtained and the OD values obtained with the three recombinant antigens and GM. The best correlation with the number of precipitin bands was obtained with the DPPV OD values with an r value of 0.6 (FIG. 2) whereas values of 0.38, 0.31 and 0.28 were respectively obtained with RNU, GM and CAT.

A kinetic analysis of 13 patients from Toulouse hospital illustrated the variations seen among patients in the antibody titers against the 4 discriminative antigens (FIG. 3 as an example of 4 patients). Although overall there was a significative difference between the aspergilloma and control patients (FIG. 1), the antibody response depended both on the patient and on the antigen. First, the levels of antibody directed against individual antigens varied with the patient. For example, for patient Maz, the highest OD value was associated to a response against CAT and DPPV whereas the lowest OD values were obtained with these 2 antigens in patient Ber. Second, the level of antibody could also vary over time depending on the antigen and on the patient. For example in patient Ben, the levels of antibody against antigen RNU increased whereas in the same patient, the level of antibody against the three other antigens tested remained constant overtime (FIG. 3).

2. ABPA

ABPA is a major complication of both cystic fibrosis patients as well as non-cystic fibrosis patients. Cystic fibrosis patients are often colonized by *Aspergillus* and this colonization may be associated to high levels of anti-*Aspergillus* antibodies which makes difficult the differentiation between patients that were colonized from true ABPA patients in this cystic fibrosis population. For this reason the inventors analysed 4 populations of patients: controls without cystic fibrosis, controls with cystic fibrosis, ABPA without cystic fibrosis and ABPA with cystic fibrosis.

FIG. 4 shows that the inventors' ELISA was able to differentiate ABPA patients from control patients in both atopic or cystic fibrosis populations. Pooling all antibody data together in a canonical plot showed the stringent separation of the 4 different populations (FIG. 5). Like in the aspergilloma patients, the 3 most discriminative antigens were RNU, CAT and DPPV in all clinical centers (Table 3).

This study confirmed that cystic fibrosis patients had high levels of anti-*Aspergillus* antibodies against all antigens and especially against the DPPIV. This result was in agreement with the fact that all cystic fibrosis patients harbour permanently *A. fumigatus*. These antibody titers remained however lower than the anti-*Aspergillus* titers found in the ABPA patients. These data suggested that the monitoring of antibody titers during the follow up of the cystic fibrosis patients could be used to identify the worsening of the colonisation or/and the rise of an ABPA pathological situation. Table 4 showed the specificity, sensitivity and negative and predictive values for ABPA for the cystic fibrosis population analysed. When each of the 3 discriminant antigens was considered separately, the lowest sensitivity value (38%) was obtained with CAT. The highest diagnostic parameter values were obtained with a combination of RNU and DPPV. Accordingly, these two antigens were considered the most valuable antigens for the diagnosis of ABPA. Similar data were found when the ABPA population was analysed in a non-cystic fibrosis background (data not shown).

As for the aspergilloma patients, significant variations in antibody titers against an antigen were seen among patients and over time in the same patient (FIG. 6). For example, patient Aud had a low anti-DPPV titer whereas patient Del had a low anti-RNU titer; in contrast patient Aub had high levels of antibody titers against RNU. Levels of antibodies were constant in patients Aub and Del but highly variable in patient Aud. Increase in antibody titers seemed to be associated to ABPA episodes whereas a decrease in the antibody titer were correlated to an improvement of the patient (FIG. 6).

3. Invasive Aspergillosis

Since the most discriminant antigens that indicated a pathological situation in the immunocompetent or atopic population were RNU, CAT and DPPV, these 3 antigens were tested to investigate the antibody situation in invasive aspergillosis. In addition, antibodies directed against GM were analysed since they have been both associated to fungal growth in the lung tissues of aspergilloma patients (see above) and suggested to be responsible for false negatives obtained with the Platelia kit used for the diagnosis of IA that is based on the detection of galactomannan antigenemia (Hearn et al., 1995, J. Clin. Microbiol. 33:982-986; Herbrecht et al., 2002, J. Clin. Oncol. 20:1898-906). The antibody levels against these 4 antigens were measured in a cohort of immunocompromised patients with proven and probable IA and controls that were submitted to the same clinical treatment but did not have a fungal infection.

First of all comparison of the serum titers in the same patients after graft or immunosuppression and after clinical IA diagnosis showed the lack of increase in antibody levels during the course of IA in these immunocompromised patients (p value of 0.83 for an error df of 118). This result confirmed that in the inventors' study, immunocompromised patients with IA did not produce detectable antibodies directed against the fungus during the development of the disease. In contrast to the antibody levels towards CAT, RNU, DPPV or GM, the level of circulating galactomannan in the same sera was discriminative, of IA with an increase in the amount of antigen released during the evolution of IA overtime (p value< 0.01 for an error df of 118).

Although the level of antibody did not change during the course of the disease, the analysis of the antibody response in the population of patients with proven IA showed that a high level of antibodies against the four antigens tested was positively correlated to the occurrence of proven/probable invasive aspergillosis. Table 5 showed that the most discriminant antigen was CAT and to a less extent DPPV. RNU and GM were poorly discriminant (see the low sensitivity values for these 2 antigens in Table 5) were identified. FIG. 7 shows the hierarchical clustering based on OD values with CAT and DPPV antigens obtained with the patient sera tested: two groups of patients containing respectively 10 (group a) and 13 patients (group b) were clearly differentiated. The OD values noted with the group of patients with low titers (b) were not significantly different from the control group (c). In contrast, the OD values in the second group of patients with high antibody titers (a) were significantly different from the other groups b and c (FIG. 8). The best sensitivity and specificity values obtained for the population a (10 patients) vs control population (34 patients) was respectively 89 and 70% for DPPV and 100 and 97% for CAT. Anti-*A. fumigatus* antibody detection in this subpopulation of patients was extremely predictive of IA. The presence of high levels of antibodies in the sera of these patients before immunosuppression suggested they were infected before graft or immunosuppressive treatments. Using the partition platform of the JMP software on the OD values obtained under our experimental ELISA conditions and with the population sampled here, the OD values indicative of a negative serum for the 4 antigens was respectively 0.21, 0.12, 0.44 and 0.54 for RNU, DPPV, CAT and GM. Values above 0.36, 0.35, 1.08 and 1.05 for the same antigens was indicative of an *Aspergillus* infection. Logistic regression data have confirmed mat the most discriminant antigens with a p value < 0001 were CAT and DPPV (data not shown).

As with the immunocompetent patients, an important variability was seen in the response of each patient to the different antigens. FIG. 9 shows examples of the evolution of the antibody and antigen response in 6 different patients. In patient PIE, BAR and RUD from the group as defined above, the antigens inducing the highest reactivity were GM, CAT and DPPV respectively. Patient GOR had high levels of antibody against RNU and GM and low levels against CAT and DPPV. Although in patients GOR or PIE shown in FIG. 9, low levels of antigenic galactomannan in the circulating fluid seems associated to high anti-GM antibody titers, the correlation coefficient obtained between anti-GM antibodies and the Platelia index in patients with proven IA was −0.04 with a non significantive p value of 0.22 for a df of 172. In the present study, negative results in IA Platelia were not directly associated with the presence of anti-GM antibodies.

These data showed that a sensitive measure of the level of antibody in the patient sera prior immunosuppression had a good positive predictive value for IA (FIG. 10). This conclusion is seen when the proven and control patients were analysed. There is also a trend towards the separation of the probable and control populations based on antibody levels suggesting that some of the probable patients are true IA.

III. Discussion

This study of the antibody response of different classes of aspergillosis patients with an ELISA format has shown the important diagnostic potential of 3 recombinant antigens that are the ribonuclease, the dipeptidylpeptidase V and the mycelial catalase 1 previously characterized in the inventors' laboratory (Beauvais et al., 1997, Infect. Imm. 65:3042-3047; Calera et al., 1997, Infect Immun. 65:4718-4724; Latgé, J., 1999, Clin. Microbiol. Rev. 12:310-350; Paris, S. et al., 1993, FEMS Microbiol. Lett. 111:31-36).

If the 3 antigens can be used in the diagnosis of aspergilloma, ABPA and IA, the respective potential of each of these 3 antigens depends on the population analysed. Catalase was the most useful antigen in both immunocompetent and immunocompromised populations. In aspergilloma patients, RNU and DPPV antigens were as or more discriminant than CAT. In ABPA patients, the most discriminant antigens were RNU and DPPV. In patients with IA, RNU was not an appropriate antigen whereas DPPV and overall CAT were the antigens recognized in most cases. In addition, the follow up of patients with aspergillosis showed that the level of antibodies directed against every antigen varied with the patient and that the major diagnostic antigen was often different in different patients. It is unknown to date if this result was due to a genetic variation in the B-cell population of the different patients or if it is associated to the infective fungal strains that would produce different amounts of the respective antigens in vivo. Lower sensitivity and positive predictive values were obtained with ABPA patients than in aspergilloma patients. This result was in agreement with the difficulty to diagnose this pathology The association of at least two and best three of the ribonuclease, catalase and dipeptidylpeptidase antigens will be optimal for the diagnosis of the most important and life-threatening aspergillosis viz aspergilloma, ABPA and invasive pulmonary aspergillosis.

In the cystic fibrosis control population, high titers of anti-*Aspergillus* antibodies were found. This result was in agreement with the common continuous colonization of these patients with *A. fumigatus*. Interestingly, the level of antibody against the DPPIV protein was higher in the cystic fibrosis control population than in the ABPA patients in the non-cystic fibrosis population suggesting that this antigen, that is homologous of the CD26, may play a role in the cystic fibrosis pathology. The inventors' study showed that ABPA can be diagnosed either in an atopic or in a cystic fibrosis population only by the quantification of specific anti-*Aspergillus* antibodies. Publications by the group of Crameri did not identify the same antigens for the diagnosis of ABPA (Hemmann et al., 1999, J. Allergy Clin. Immunol. 104:601-607). Antigen selection by the Crameri's laboratory was based on a phage display system and the CAT and DPPV antigens are high Mr protein antigens that may have been under represented in Crameri's library. This seems the case since a collaborative study with R. Crameri has shown that ABPA patients from Davos react significantly with RNU, CAT and DPPV (Crameri, personal communication). In addition, in Crameri's studies, primary selection was based on IgE binding whereas our analysis considered IgG levels and it is known for APBA that specific anti-*Aspergillus* IgE and IgG may recognize different epitopes in these patients.

The most important discovery of the inventors' study was the presence of high titers of anti-*Aspergillus* antibodies in about half of the patients to be transplanted. A few previous publications have also reported the presence of anti-*Aspergillus* antibodies in immunocompromised patients with IA (Hearn et al., 1995, J. Clin. Microbiol. 33:982-986; Herbrecht et al., 2002, J. Clin. Oncol. 20:1898-906). The lack of increase of antibody levels during the course of the disease in the patients examined in this study, suggested that the occurrence of antibodies is not a response of the patient to the fungal infection. In contrast, it suggested that a significant portion of the patients to be submitted to an immunosuppressive therapy was indeed harbouring an *Aspergillus* infection at their entrance to the hospital. Interestingly, earlier epidemiological studies by the inventors' group (Chan et al., 2002, J. Clin. Microbiol. 40:2041-2045; Debeaupuis et al., 1995, Can. J. Bot. 73:1087-1091) have shown that the origin of IA was nosocomial in about 50% of the cases. This antibody detection study suggested that about 50% (10/23 patients) of the patients with IA were infected at the entrance at the hospital. These results are of the most interest for patients at risk for IA because they suggest the possibility of colonization before immunosuppression and that this hidden *Aspergillus* infection can be now suspected as an origin of IA for a significant number of patients. Looking for antibodies will become then an essential screening to perform before starting an intensive immunotherapy and subsequent graft. All these findings will influence greatly the management of the patients prior to immunosuppression since attempts can be made to eliminate the fungus from the lungs. The importance of an anti-*Aspergillus* antibody test in the immunocompromised setting is also reinforced by the displacement of the peak of IA towards the $6^{th}$ month after graft (Morgan et al., 2004, Med. Mycol. 00:1-10), and by the occurrence of in immunocompetent patients from intensive care units (Meersseman et al., 2004, Crit. Care Med. 170:621-625).

Previous studies have reported that the presence of high amounts of antibodies could be associated to the clearance of the circulating antigens in fungal infections of the immunocompromised patient Such findings have been repeatedly seen in *Candida* infections where low antigen levels could be associated to high mannan antibodies concentration (Sendid et al., 2003, J. Clin. Microbiol. 41:4551-4558; Sendid et al, 1999, J. Clin. Microbiol. 37:1510-1517). In *Aspergillus* infections several studies have also suggested that false-negative antigenemia tests could be due to the presence of a high level of anti-Galactomannan antibodies in the serum (Herbrecht et al., 2002, J. Clin. Oncol. 20:1898-906; Man et al, 2004, J. Infect Dis. 190:641-649; Pinel et al., 2003, J. Clin. Microbiol. 41:2184-2186). Although in the inventors' study the presence of antibodies against GM seems correlated with a low titer of antigens in a few sera, no statistical significant negative correlation could be demonstrated between the GM antigen and anti-GM antibody concentrations. For some IA false negative patients, low level of GM and anti-GM antibodies were both found. These false-negative data remain unexplained but it excluded or at least minimize the responsibility of antibodies for creating false negatives in the Platelia kit.

All these findings will influence greatly the management of the patients prior to immunosuppression in view to cure or remove the fungus. An hidden *Aspergillus* infection as an origin of IA can be now suspected for a significant number of patients.

TABLE 1

Materials used for the production of *A. fumigatus* antigens in *P. pastoris*.

| Gene | GeneBank accession no | Amplification primers[a] | Orien- tation | Enclosed amino acid sequences[b] | PCR product with cloning sites[c] | Cloning vector with cloning and (linearization) sites |
|---|---|---|---|---|---|---|
| RNU | X85092 | 7[d]: GTTC/TCGAGTCCCTGTGGTCCAGCCGCGC | 5'-3' | 17: (R)VPVVQPR | PEP(61-1185) XhoI-BamHI | pKJ113 XhoI-BamHI (SmaI) |
|  |  | 8: TCCG/GATCCCTA(GTGATG)$_3$TGCCTGAGGG GCGAAGCCGAG | 3'-5' | 18: LGFAPQAH$_6$* |  |  |
|  | Z11580 | 9: CTGC/TCGAGCGCCTGTCCAGGAAACTGT | 5'-3' | 19: (R)APVQETR | ALP(61-1209) XhoI- | pKJ113 |
|  |  | 10: AGCG/GATCCCTA(GTGATG)$_3$AGCATTGC CATTGTAGGCAAG | 3'-5' | 20: LAYNGNAH$_6$* | BamHI | XhoI-BamHI (EcoRI) |
|  | Z30424 | 11: CTGTTT/AAACATCCCGCTCACCAGTCTT AC | 5'-3' | 21: (K)HPAHQSY | MEP(55-1899) DraI- | pKJ111 |
|  |  | 12: GTCTTT/AAACTA(GTGATG)$_3$ACAGACA CCACTGGGGACCTC | 3'-5' | 22: EVPSGVCH$_6$* | DraI | SmaI (BglII) |
|  | U87950 | 13: TGCGAT/ATCGCCATTGACGTCCCTCG TCAACCA | 5'-3' | 23: (IA)IDVPRQP | DPPIV(43-2295) | pKJ111 SmaI (BglII) |
|  |  | 14: TGCGAT/ATCCTA(GTGATG)$_3$CAGAA CAGACTTCTTGCTCCA | 3'-5' | 24: WSKKSVLH$_6$* | EcoRV-EcoRV |  |

TABLE 1-continued

Materials used for the production of A. fumigatus antigens in P. pastoris.

| Gene no | Amplification primers[a] | Orientation | Enclosed amino acid sequences[b] | PCR product with cloning sites[c] | Cloning vector with cloning and (linearization) sites |
|---|---|---|---|---|---|
| L48074 | 5: GCG/AATTCCTTACACCTGAGCAGCTAATC<br>6: GCA/GATCTA(GTGATG)₃GTTATAATTCACAACCGGGAC | 5'-3'<br>3'-5' | 25: (EF)LTPEQLI<br>26: VPVVNYNH₆* | DPPV(55-2163)<br>EcoRI-BglII | pHILS1<br>EcoRI-BamHI<br>(BglII) |
| M55508 | 1: TAGC/TCGAGCCTCGCCCCTCGACGCT<br>2: ACCG/GATCCCTA(GTGATG)₃AGAACACAGTCTCAAGTC | 5'-3'<br>3'-5' | 27: (RA)SPLDA<br>28: DLRLCSH₆* | RNU(64-528)<br>XhoI-BamHI | pKJ113<br>XhoI-BamHI<br>(EcoRI) |
| U97574 | 3: AATGC/TCGAGTATGTCCCTATATGACCGGC<br>4: GGTA/GATCTCTA(GTG)₆ATCCACGGGAAACCGGTC | 5'-3'<br>3'-5' | 29: (R)VCPYMTG<br>30: DRFPVDH₆* | CAT(46-2010)<br>XhoI-BglII | pKJ111<br>XhoI-BamHI<br>(BglII) |
| AF128886 | 15: CAAC/TCGAGAAAGAGTCAAGGCTGTTGCTGTCCTC<br>16: TAAGC/GGCCGCATTA(GTGATG)₃AGCGGCGATACCAATGAC | 5'-3'<br>3'-5' | 31: VKAVAVL<br>32: VIGIAAH₆* | SOD(4-1386)<br>XhoI-NotI | pPICZαA<br>XhoI-NotI<br>(DraI) |

[a]Slashes indicate restriction endonuclease cleavage sites.
[b]In parentheses are shown amino acids encoded by the recognition site sequence and added to the N-terminal extremity of A. fumigatus antigens; asterisks indicate stops.
[c]The numbers in parentheses represent the nucleotide position of amplification products on A. fumigatus antigen cDNAs.
[d]The heavy type number represents the corresponding SEQ ID NO identifier.

TABLE 2

Efficiency of the ribonuclease (RNU), catalase (CAT) and dipeptidylpeptidase V (DPPV) in the diagnosis of aspergilloma by ELISA. Number of patients are presented in the upper part of the table; sensitivity specificity, positive and predictive values are estimated in % calculated on patient's response. Data from 3 centers pooled; 1 serum per patient randomly selected when several sera were available per patient

|  | RNU | DPPV | CAT | CAT + RNU | CAT + DPPV | RNU + DPPV | RNU + DPPV + CAT |
|---|---|---|---|---|---|---|---|
| True negative | 40 | 40 | 40 | 39 | 39 | 39 | 38 |
| False positive | 1 | 1 | 1 | 2 | 2 | 2 | 3 |
| True positive | 46 | 45 | 44 | 53 | 53 | 52 | 54 |
| False negative | 11 | 12 | 13 | 4 | 4 | 5 | 3 |
| Sensitivity | 81% | 79% | 77% | 93% | 93% | 91% | 95% |
| Specificity | 98% | 98% | 98% | 95% | 95% | 95% | 93% |
| Positive predictive value (PPV) | 78% | 77% | 75% | 91% | 91% | 89% | 93% |
| Negative predictive value (NPV) | 98% | 98% | 98% | 96% | 96% | 96% | 95% |

TABLE 3

Student's test data showing the discriminative antigens for the diagnosis of ABPA in patients with or without cistic fibrosis

| Level | |
|---|---|
| cf-abpa, DPPIV | A |
| cf, DPPIV | B |
| abpa, DPPIV | BC |
| cf-abpa, DPPV | BC |
| abpa, RNU | BCD |
| cf-abpa, CAT | CDE |
| cf-abpa, SOD | CDEF |
| cf-abpa, RNU | CDEF |
| abpa, CAT | CDEFG |
| control, DPPIV | CDEF |
| abpa, SOD | CDEFGH |
| abpa, DPPV | DEFGHI |
| cf, SOD | EFG |
| cf-abpa, MEP | EFGHIJK |
| control, SOD | FGHIJK |
| cf, CAT | GHI K |
| cf, MEP | IJKL |
| cfabpa, PEP | HIJKLMN |
| abpa, MEP | HIJKLMNO |
| cf, PEP | J LM |
| abpa, PEP | JKLMNOP |

TABLE 3-continued

Student's test data showing the discriminative antigens for the diagnosis of ABPA in patients with or without cistic fibrosis

| Level | |
|---|---|
| control, MEP | LMNO |
| cf, RNU | LMNO |
| cf, DPPV | LMNO |
| control, PEP | MNOP |
| control, CAT | NOP |
| control, DPPV | OP |
| control, RNU | P |

Levels not connected by same letter are significantly different

TABLE 4

Results of the antibody determination against the 3 antigens RNU, CAT and DPPV considered separately or together in ABPA and control patients in cystic fibrosis population (same legend as in table 2)

| | RNU | DPPV | CAT | CAT + RNU | CAT + DPPV | RNU + DPPV | RNU + DPPV + CAT |
|---|---|---|---|---|---|---|---|
| True negative | 50 | 48 | 50 | 49 | 48 | 47 | 47 |
| False positive | 1 | 3 | 1 | 2 | 3 | 4 | 4 |
| True positive | 8 | 12 | 6 | 9 | 12 | 14 | 14 |
| False negative | 8 | 4 | 10 | 7 | 4 | 2 | 2 |
| Sensitivity | 50% | 75% | 38% | 56% | 75% | 88% | 88% |
| Specificity | 98% | 94% | 98% | 96% | 94% | 92% | 92% |
| Positive predictive value (PPV) | 86% | 92% | 83% | 88% | 92% | 96% | 96% |
| Negative predictive value (NPV) | 89% | 80% | 86% | 82% | 80% | 78% | 78% |

TABLE 5

Efficiency of the ribonuclease (RNU), catalase (CAT), dipeptidylpeptidase V (DPPV) and galactomannan (GM) in the diagnosis of IA patients.

| | RNU | DPPV | CAT | GM |
|---|---|---|---|---|
| True negative | 35 | 34 | 26 | 35 |
| False positive | 0 | 1 | 9 | 0 |
| True positive | 3 | 7 | 18 | 4 |
| False negative | 20 | 16 | 5 | 19 |
| Sensitivity | 13% | 30% | 78% | 17% |
| Specificity | 100% | 97% | 74% | 100% |
| Positive predictive value (PPV) | 64% | 68% | 84% | 65% |
| Negative predictive value (NPV) | 100% | 88% | 67% | 100% |

Calculations were made based on the antibody response of the patients at their entrance at the hospital before immunosuppressive therapy (same legend as in table 2).

The invention claimed is:

1. A method for the in vitro diagnosis of an *Aspergillus* infection which comprises:
   a) incubating serum or plasma sample of a subject with *Aspergillus* antigens for the formation of immunocomplexes susceptible to be obtained between antibodies and the antigens, and
   b) determining the quantity of the antibodies directed against the *Aspergillus* antigens,
      wherein the *Aspergillus* antigens are selected from the group consisting of a combination of at least two the following antigens:
      the ribonuclease (RNU) antigen,
      the catalase (CA) antigen, and
      the dipeptidylpeptidase V (DPPV) antigen.

2. The method of claim 1, which further comprises:
   c) incubating a negative reference serum or plasma sample with the *Aspergillus* antigens for the formation of immunocomplexes susceptible to be obtained between antibodies and the antigens,
   d) determining the quantity of antibodies in the negative reference sample or plasma sample directed against the *Aspergillus* antigens, and
   e) comparing the quantity of antibodies from step (b) with the quantity of antibodies from step (d), a difference in the quantities of antibodies being indicative of an *Aspergillus* infection.

3. The method of claim 1 or 2, wherein the *Aspergillus* antigens are coated on a solid support.

4. The method of claim 3, wherein each of said antigens is coated in a different location on the solid support.

5. The method of claim 4, wherein the solid support is an enzyme linked immunosorbent assay (ELISA) plate, and the method comprises:
   a) incubating said serum or plasma sample with the *Aspergillus* antigens coated on the ELISA plate,
   b) eliminating from the ELISA plate the antibodies of said serum or plasma sample not bound to the *Aspergillus* antigens,
   c) contacting anti-immunoglobulin (anti-Ig) antibodies conjugated with an enzyme, said anti-Ig antibodies being capable to bind to the antibodies of said serum or plasma sample,
   d) eliminating from the ELISA plate the anti-Ig antibodies not bound to the antibodies of said serum or plasma sample,
   e) adding the corresponding soluble substrate for the enzyme, and
   f) reading the absorbance values of the wells of the ELISA plate in an ELISA reader at an appropriate wavelength, wherein the quantity of said antibodies is determined by means of the obtained absorbance values.

6. The method of claim 3, wherein the *Aspergillus* antigens comprise the combination of the RNU and CA antigens.

7. The method of claim 3, wherein the *Aspergillus* antigens comprise the combination of the RNU and DPPV antigens.

8. The method of claim 3, wherein the *Aspergillus* antigens comprise the combination of the CA and DPPV antigens.

9. The method of claim 3, wherein the *Aspergillus* antigens comprise the combination of the RNU, CA and DPPV antigens.

10. The method of claim 3, wherein at least one of the RNU, CA, and DPPV *Aspergillus* antigens is a recombinant antigen.

11. The method of claim 10, wherein the at least one recombinant *Aspergillus* antigen is obtained by cloning the amplification product of the corresponding cDNA in an expression vector.

12. The method of claim 11, wherein the amplification product of the corresponding cDNA is obtained from an *Aspergillus fumigatus* cDNA library using a couple of primers specific for said at least one *Aspergillus* antigen.

13. The method of claim 12, wherein the couple of primers specific for the RNU antigen is SEQ ID NO:1 and SEQ ID NO:2.

14. The method of claim 12, wherein the couple of primers specific for the CA antigen is SEQ ID NO:3 and SEQ ID NO:4.

15. The method of claim 12, wherein the couple of primers specific for the DPPV antigen is SEQ ID NO:5 and SEQ ID NO:6.

16. The method of claim 3, wherein the *Aspergillus* antigens further comprise galactomannan (GM) antigen.

17. The method of claim 16, wherein the GM antigen is obtained by purification from an *Aspergillus* culture.

18. The method of claim 3, wherein a unique profile of detection signals for a given *Aspergillus* strain is determined.

19. The method of claim 18, which further comprises comparing the detection signal profile with a standard profile for each *Aspergillus* strain, allowing identification of the strain infecting the subject.

20. The method of claim 3, wherein the *Aspergillus* infection has led to aspergilloma and/or allergic bronchopulmonary *aspergillus* (ABPA).

21. The method of claim 20, wherein the *Aspergillus* infection leading to ABPA is diagnosed in a subject suffering from cystic fibrosis as well as in a subject not suffering from cystic fibrosis.

22. The method of claim 3, wherein the *Aspergillus* infection is an invasive aspergillosis which it is possible to diagnose before immunosuppression in the subject to be grafted.

23. The method of claim 3, which allows the diagnosis of the *Aspergillus* infection in an immunocompromised human being.

24. A diagnostic kit for determining in a serum or plasma sample a quantity of antibodies directed against *Aspergillus* antigens, comprising:

(a) a combination consisting of at least two of the following isolated *Aspergillus* antigens:
recombinant RNU antigen,
recombinant CA antigen, and
recombinant DPPV antigen.

25. The diagnostic kit of claim 24, which further comprises a solid support on which said *Aspergillus* antigens are coated.

26. The diagnostic kit of claim 24 or 25, which further comprises a solution containing anti-Ig antibodies conjugated with a marker.

27. The diagnostic kit of claim 24 or 25, which further comprises a washing buffer.

28. The diagnostic kit of claim 24 or 25, wherein the *Aspergillus* antigens consist of the combination of the RNU, CA, and DPPV antigens.

29. The diagnostic kit of claim 24 or 25, wherein the *Aspergillus* antigens further comprise GM antigen.

30. The diagnostic kit of claim 25, wherein the solid support is an ELISA plate and the marker is an enzyme.

31. The diagnostic kit of claim 30, which further comprises a solution containing a corresponding soluble substrate for the enzyme.

* * * * *

UNITED STATES PATENT AND TRADEMARK OFFICE
CERTIFICATE OF CORRECTION

| | | |
|---|---|---|
| PATENT NO. | : 7,888,041 B2 | Page 1 of 1 |
| APPLICATION NO. | : 11/988038 | |
| DATED | : February 15, 2011 | |
| INVENTOR(S) | : Anne Beauvais et al. | |

It is certified that error appears in the above-identified patent and that said Letters Patent is hereby corrected as shown below:

Claim 1, col. 31, line 34, "at least two the" should read --at least two of the--.

Signed and Sealed this
Twenty-sixth Day of April, 2011

David J. Kappos
*Director of the United States Patent and Trademark Office*

SEQUENCE LISTING

<160> NUMBER OF SEQ ID NOS: 33

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tagctcgagc ctcgcccctc gacgct                                          26

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgaactctg acacaagagt agtggtagtg gtagtgatcc ctaggcca                  48

-continued

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatgctcgag tatgtccta tatgaccggc                                    30

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggccaaag ggcacctagt ggtggtggtg gtggtgatct ctagatgg               48

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgaattcct tacacctgag cagctaatc                                    29

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagggccaac acttaatatt ggtagtggta gtggtagtga tctagacg               48

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttctcgagt ccctgtggtc cagccgcgc                                    29

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagccgaagc ggggagtccg tgtagtggta gtggtagtga tccctaggcc t           51

<210> SEQ ID NO 9
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgctcgagc gcctgtccag gaaactcgt                                      29

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaacggatgt taccgttacg agtagtggta gtggtagtga tccctaggcg a             51

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgtttaaac atcccgctca ccagtcttac                                     30

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctccaggggt caccacagac agtagtggta gtggtagtga tcaaatttct g             51

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgcgatatcg ccattgacgt ccctcgtcaa cca                                 33

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acctcgttct tcagacaaga cgtagtggta gtggtagtga tcctatagcg t             51

<210> SEQ ID NO 15
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caactcgaga aaagagtcaa ggctgttgct gtcctc                                36

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagtaaccat agcggcgagt agtggtagtg gtagtgatta cgccggcgaa t               51

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Val Pro Val Val Gln Pro Arg
1               5

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gly Phe Ala Pro Gln Ala His His His His His His
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Pro Val Gln Glu Thr Arg
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ala Tyr Asn Gly Asn Ala His His His His His His
1               5                   10
```

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys His Pro Ala His Gln Ser Tyr
1               5

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Val Pro Ser Gly Val Cys His His His His His His
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Ala Ile Asp Val Pro Arg Gln Pro
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Ser Lys Lys Ser Val Leu His His His His His His
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Phe Leu Thr Pro Glu Gln Leu Ile
1               5

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Val Pro Val Val Asn Tyr Asn His His His His His
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Ser Pro Leu Asp Ala
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Leu Arg Leu Cys Ser His His His His His His
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Val Cys Pro Tyr Met Thr Gly
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Phe Pro Val Asp His His His His His His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Lys Ala Val Ala Val Leu
1               5

<210> SEQ ID NO 32
<211> LENGTH: 12
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 32

Val Ile Gly Ile Ala Ala His His His His His His
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 33

His His His His His His
1               5
```